United States Patent
Song et al.

(10) Patent No.: US 11,253,229 B2
(45) Date of Patent: Feb. 22, 2022

(54) WIRELESS ULTRASOUND PROBE, ULTRASOUND DIAGNOSTIC APPARATUS CONNECTED TO WIRELESS ULTRASOUND PROBE, AND OPERATING METHOD OF ULTRASOUND DIAGNOSTIC APPARATUS

(71) Applicant: SAMSUNG MEDISON CO., LTD., Hongcheon-gun (KR)

(72) Inventors: Youngseuk Song, Seongnam-si (KR); Gilju Jin, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 314 days.

(21) Appl. No.: 16/427,453

(22) Filed: May 31, 2019

(65) Prior Publication Data

US 2019/0365352 A1 Dec. 5, 2019

(30) Foreign Application Priority Data

May 31, 2018 (KR) .................. 10-2018-0062895

(51) Int. Cl.
*A61B 8/00* (2006.01)
*G01S 7/00* (2006.01)

(52) U.S. Cl.
CPC .......... *A61B 8/4472* (2013.01); *A61B 8/4427* (2013.01); *A61B 8/565* (2013.01);
(Continued)

(58) Field of Classification Search
CPC ... A61B 8/4472; A61B 8/4427; A61B 8/4433; G01S 7/003
See application file for complete search history.

(56) References Cited

U.S. PATENT DOCUMENTS

| 9,622,718 B2 | 4/2017 | Watanabe |
| 10,129,926 B2 | 11/2018 | Kim et al. |

(Continued)

FOREIGN PATENT DOCUMENTS

| JP | 2000-107176 A | 4/2000 |
| JP | 2011-067544 A | 4/2011 |

(Continued)

OTHER PUBLICATIONS

Communication dated Oct. 18, 2019, issued by the European Patent Office in counterpart European Application No. 19175910.9.

*Primary Examiner* — Boniface N Nganga
(74) *Attorney, Agent, or Firm* — Sughrue Mion, PLLC

(57) ABSTRACT

Provided is a wireless ultrasound probe configured to detect a state in which the wireless ultrasound probe is detached from a charging terminal of an ultrasound diagnostic apparatus, causing supply of the charging power to the wireless ultrasound probe to be discontinued, and the wireless ultrasound probe is paired with the ultrasound diagnostic apparatus by using a wireless communication scheme when supply of the charging power is discontinued. Also provided are an ultrasound diagnostic apparatus and an operating method of the ultrasound diagnostic apparatus configured to be automatically paired with a wireless ultrasound probe in a state in which the wireless ultrasound probe is detached from a charging terminal of the ultrasound diagnostic apparatus, causing supply of the charging power to the wireless ultrasound probe to be discontinued.

14 Claims, 13 Drawing Sheets

(52) U.S. Cl.
CPC .......... *A61B 8/4433* (2013.01); *A61B 8/4483* (2013.01); *G01S 7/003* (2013.01)

(56) References Cited

U.S. PATENT DOCUMENTS

| | | |
|---|---|---|
| 2006/0068834 A1 | 3/2006 | Jones |
| 2010/0168576 A1* | 7/2010 | Poland ................. A61B 8/4427 600/443 |
| 2013/0053697 A1* | 2/2013 | Holl .................... G01S 7/52096 600/459 |
| 2013/0109973 A1 | 5/2013 | Kurokawa |
| 2014/0107487 A1 | 4/2014 | Kim et al. |
| 2014/0180110 A1* | 6/2014 | Schmedling ......... A61B 8/4472 600/447 |
| 2015/0065882 A1* | 3/2015 | Cho .................... A61B 8/5207 600/443 |
| 2015/0313578 A1 | 11/2015 | Yu et al. |
| 2016/0224085 A1 | 8/2016 | Jo et al. |
| 2017/0027541 A1 | 2/2017 | Henderson et al. |

FOREIGN PATENT DOCUMENTS

| | | |
|---|---|---|
| JP | 6147743 B2 | 6/2017 |
| KR | 10-2014-0046754 A | 4/2014 |
| KR | 10-2015-0031673 A | 3/2015 |
| KR | 10-1603071 B1 | 3/2016 |
| KR | 10-1693680 B1 | 1/2017 |
| WO | 0031563 A1 | 6/2000 |
| WO | 2008146205 A1 | 12/2008 |
| WO | 2017009735 A1 | 1/2017 |

\* cited by examiner

WIRELESS ULTRASOUND PROBE, ULTRASOUND DIAGNOSTIC APPARATUS CONNECTED TO WIRELESS ULTRASOUND PROBE, AND OPERATING METHOD OF ULTRASOUND DIAGNOSTIC APPARATUS

CROSS-REFERENCE TO RELATED APPLICATION(S)

This application is based on and claims priority under 35 U.S.C. § 119 to Korean Patent Application No. 10-2018-0062895, filed on May 31, 2018, in the Korean Intellectual Property Office, the disclosure of which is incorporated by reference herein in its entirety.

BACKGROUND

1. Field

The disclosure relates to a wireless ultrasound probe, an ultrasound diagnostic apparatus connected to the wireless ultrasound probe, and an operating method of the ultrasound diagnostic apparatus, and more particularly, to an ultrasound diagnostic apparatus configured to supply a charging power to a wireless ultrasound probe, and to activate the wireless ultrasound probe by being paired in a wireless communication manner with the wireless ultrasound probe for which supply of the charging power is discontinued.

2. Description of Related Art

An ultrasound system transmits an ultrasound signal generated by transducers of an ultrasound probe to an internal part of an object and receives information about echo signals reflected from the internal part of the object, thereby obtaining an image of the internal part of the object. In particular, the ultrasound system is used for medical purposes including observation of an internal area of an object, detection of foreign substances, diagnosis of damage to the object, imaging of characteristics, or the like.

Recently, to improve operability of an ultrasound probe by removing a communication cable for transmitting and receiving ultrasound image data between the ultrasound probe and an ultrasound diagnostic apparatus or by eliminating inconvenience due to the presence of the communication cable, a wireless ultrasound probe connected to the ultrasound diagnostic apparatus by using wireless communication is being developed. However, to obtain wireless pairing between the ultrasound diagnostic apparatus and a wireless ultrasound probe by using a current technique, a user has to select a wireless ultrasound probe to be used in examining an object and to make a separate input such as a button input, a touch input, or the like to allow the wireless ultrasound probe to transmit a pairing signal to the ultrasound diagnostic apparatus.

SUMMARY

Provided is a wireless ultrasound probe configured to detect a state in which supply of a battering charging power is discontinued from a charging terminal of an ultrasound diagnostic apparatus, and to be wirelessly paired with the ultrasound diagnostic apparatus.

Provided are an ultrasound diagnostic apparatus configured to detect a state in which supply of a charging power to a battery of a wireless ultrasound probe is discontinued, and to perform wireless pairing with the wireless ultrasound probe, and an operating method of the ultrasound diagnostic apparatus.

Additional aspects will be set forth in part in the description which follows and, in part, will be apparent from the description, or may be learned by practice of the presented embodiments.

In accordance with an aspect of the disclosure, a wireless ultrasound probe includes a battery; a wireless communication module; a charger configured to receive a charging power for charging the battery from the ultrasound diagnostic apparatus; and a controller configured to detect a state in which the charger is detached from a charging terminal of the ultrasound diagnostic apparatus to discontinue supply of the charging power, and to control the wireless communication module to be wirelessly paired with the ultrasound diagnostic apparatus.

After the wireless ultrasound probe is paired with the ultrasound diagnostic apparatus, the controller may be further configured to control the wireless communication module to transmit, to the ultrasound diagnostic apparatus, probe characteristic information including at least one of identification (ID) information of the wireless ultrasound probe, a type of the wireless ultrasound probe, a radio frequency range of use, depth value information, and remaining battery amount information.

The controller may be further configured to: detect an activation signal indicating at least one of contact between the wireless ultrasound probe and an object, application of a gel with respect to the wireless ultrasound probe, motion of a user holding the wireless ultrasound probe, and a button input with respect to the wireless ultrasound probe, and activate, in response to the activation signal, the wireless ultrasound probe to transmit an ultrasound signal to the object.

The wireless ultrasound probe may be mounted in a case, and the charger is further configured to receive, from the case, the charging power.

The controller may be further configured to detect a state in which the wireless ultrasound probe is detached from the case to discontinue supply of the charging power from the case, and control the wireless communication module to be wirelessly paired with the ultrasound diagnostic apparatus when the charging power from the case is discontinued.

In accordance with another aspect of the disclosure, an ultrasound diagnostic apparatus includes a wireless communication module; a charging power supplier configured to supply a charging power to the wireless ultrasound probe; and a controller configured to detect a state in which the wireless ultrasound probe that has been being charged is detached from the charging power supplier, causing supply of the charging power to the wireless ultrasound probe to be discontinued, and to control the wireless communication module to be wirelessly paired with the wireless ultrasound probe by using a wireless communication scheme.

In the state in which supply of the charging power to the wireless ultrasound probe is discontinued, the controller may be further configured to control the wireless communication module to receive, from the paired wireless ultrasound probe, probe characteristic information including at least one of ID information of the wireless ultrasound probe, a type of the wireless ultrasound probe, a radio frequency range of use, depth value information, and remaining battery amount information.

The ultrasound diagnostic apparatus may further include a display configured to display a user interface (UI) indicating, by using a text or an icon, the probe characteristic information received from the wireless ultrasound probe.

The ultrasound diagnostic apparatus may further include a memory storing system information and a preset of a UI pattern, the system information may be used to obtain an ultrasound image according to ID information and a type of the wireless ultrasound probe, and the preset is about a format of the ultrasound image, and the controller may be further configured to load, from the memory, the preset based on the ID information and the type of the wireless ultrasound probe which is included in the probe characteristic information, and to display the loaded preset on the display.

The wireless ultrasound probe and the ultrasound diagnostic apparatus may be mounted in a case, and the wireless ultrasound probe may receive, from the case, a charging power for charging a battery of the wireless ultrasound probe.

The controller may be further configured to detect a state in which the wireless ultrasound probe is detached from the case to discontinue supply of the charging power from the case, and control the wireless communication module to be wirelessly paired with the wireless ultrasound probe when the charging power from the case is discontinued.

The controller may be further configured to detect an activation signal indicating at least one of contact between the wireless ultrasound probe and an object, application of a gel with respect to the wireless ultrasound probe, motion of a user holding the wireless ultrasound probe, and a button input with respect to the wireless ultrasound probe, and transmit, in response to the activation signal, a beamforming control signal to the wireless ultrasound probe to transmit an ultrasound signal to the object.

In accordance with another aspect of the disclosure, a method, performed by an ultrasound diagnostic apparatus, of connecting the ultrasound diagnostic apparatus with a wireless ultrasound probe includes supplying a charging power to the wireless ultrasound probe; detecting a state in which the wireless ultrasound probe is detached to discontinue supply of the charging power to the wireless ultrasound probe; and performing pairing with the wireless ultrasound probe by using a wireless communication scheme.

The method may further include, in the state in which supply of the charging power to the wireless ultrasound probe is discontinued, receiving, from the paired wireless ultrasound probe, probe characteristic information including at least one of ID information of the wireless ultrasound probe, a type of the wireless ultrasound probe, a radio frequency range of use, depth value information, and remaining battery amount information.

The method may further include displaying a UI indicating, by using a text or an icon, the probe characteristic information received from the wireless ultrasound probe.

The method may further include loading, from a memory of the ultrasound diagnostic apparatus, system information and a preset of a UI pattern, wherein the system information is used to obtain an ultrasound image according to the ID information and the type of the wireless ultrasound probe which are included in the probe characteristic information, and the preset is about a format of the ultrasound image; and displaying the loaded preset.

The wireless ultrasound probe and the ultrasound diagnostic apparatus may be mounted in a case, and the wireless ultrasound probe may receive, from the case, a charging power for charging a battery of the wireless ultrasound probe.

The detecting of the state may include detecting a state in which the wireless ultrasound probe is detached from the case to discontinue supply of the charging power from the case, and the performing of the pairing may include performing wireless pairing with the wireless ultrasound probe when supply of the charging power from the case to the wireless ultrasound probe is discontinued.

The method may further include, after the pairing, detecting an activation signal indicating at least one of contact between the wireless ultrasound probe and an object, application of a gel with respect to the wireless ultrasound probe, motion of a user holding the wireless ultrasound probe, and a button input with respect to the wireless ultrasound probe; and activating, in response to the activation signal, the wireless ultrasound probe to transmit an ultrasound signal to the object.

In accordance with another aspect of the disclosure, a non-transitory computer-readable recording medium having recorded thereon a program to be executed on a computer includes instructions to perform supplying a charging power to a wireless ultrasound probe; detecting a state in which the wireless ultrasound probe is detached from a charging terminal of an ultrasound diagnostic apparatus to discontinue supply of the charging power to the wireless ultrasound probe; and performing wireless pairing between the ultrasound diagnostic apparatus and the wireless ultrasound probe.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1A:
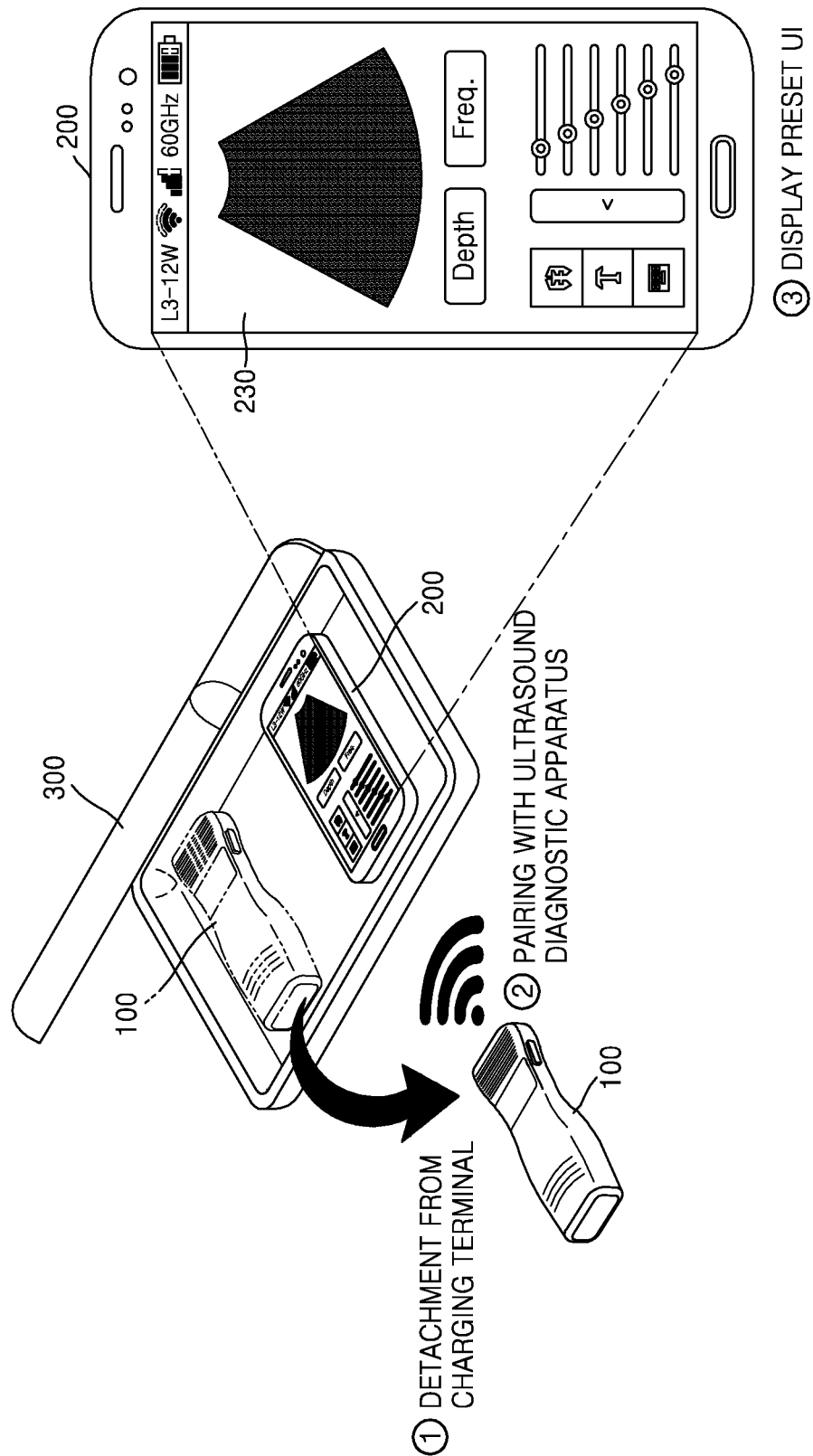
FIGS. 1A and 1B are diagrams illustrating an embodiment in which an ultrasound diagnostic apparatus is connected to a wireless ultrasound probe for which charging is discontinued, and displays state information of the connected wireless ultrasound probe, according to an embodiment.

Advantages and features of one or more embodiments of the present disclosure and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present disclosure to one of ordinary skill in the art, and the present disclosure will only be defined by the appended claims.

Terms used herein will now be briefly described and then one or more embodiments of the present disclosure will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present disclosure means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

In the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a medical image expert, who uses an ultrasound diagnostic apparatus, or a technician who repairs a medical apparatus.

In the present specification, terms "first", "second", or "first-1" are used to indicate different components, different objects, different images, different pixels, or different patches. Therefore, the terms "first", "second", or "first-1" should not be considered to indicate an order of components or to indicate that one component dominates other components.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail so as not to obscure the embodiments with unnecessary detail.

Figure 1B:
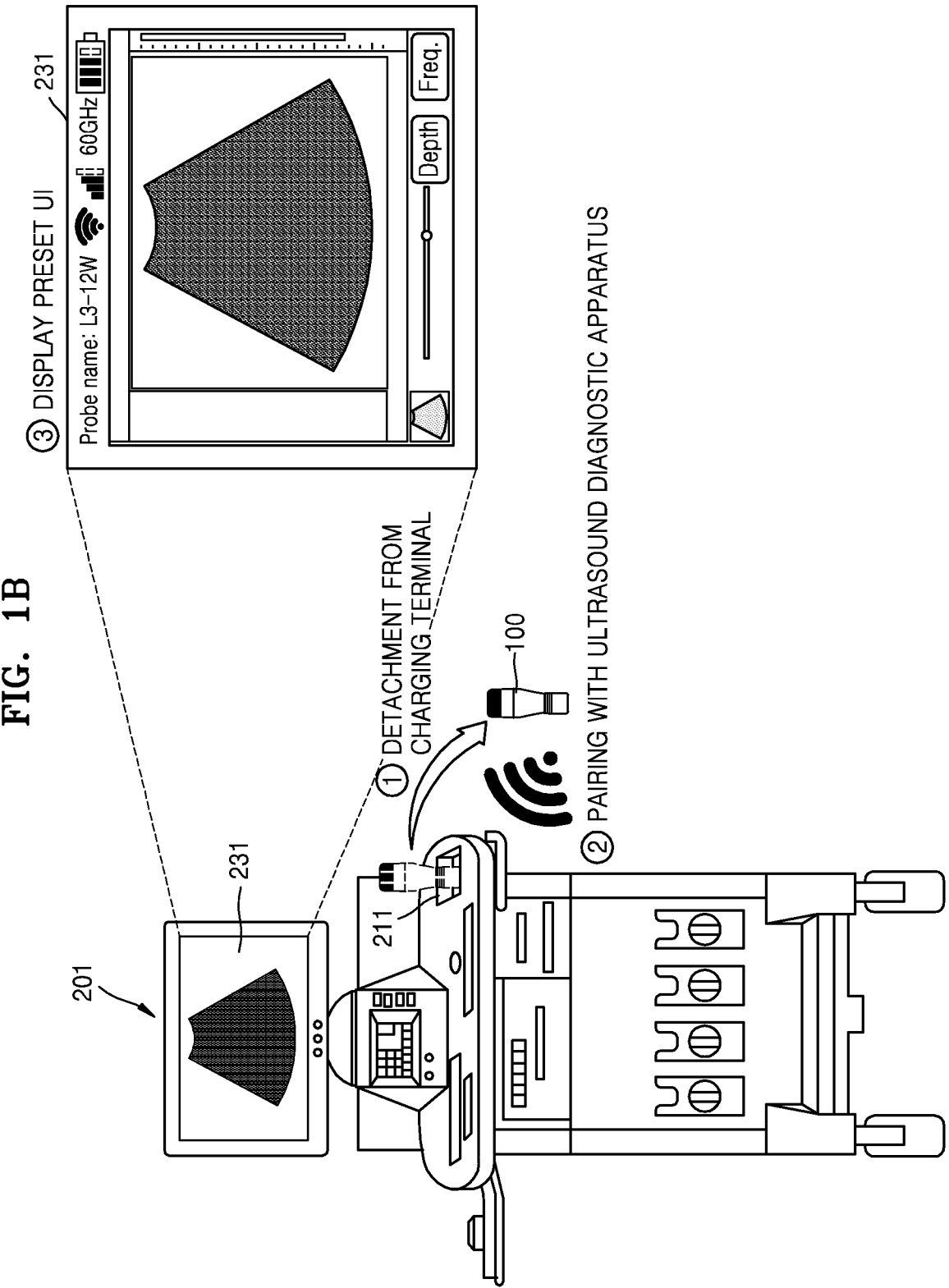

FIGS. 1A and 1B are diagrams illustrating an embodiment in which a wireless ultrasound probe 100 according to an embodiment is detached from a charging terminal and then is paired with an ultrasound diagnostic apparatus 200, and the ultrasound diagnostic apparatus 200 displays a preset user interface (UI), based on pairing information received from the wireless ultrasound probe 100.

Referring to FIG. 1A, the wireless ultrasound probe 100 and the ultrasound diagnostic apparatus 200 may be placed in a case 300 and may receive a charging power from the case 300. The wireless ultrasound probe 100 may include a battery, and may receive the charging power to charge the battery from the case 300. In an embodiment, the wireless ultrasound probe 100 may charge the battery by receiving the charging power from the case 300 by using a wired charging method using a cable or by using a wireless charging method using a wireless charging pad, a wireless charging coil, or the like.

Referring to FIG. 1A, the ultrasound diagnostic apparatus 200 may be embodied as a portable-type ultrasound diagnostic apparatus. For example, the ultrasound diagnostic apparatus 200 may include, but is not limited to, a picture archiving and communication system (PACS) viewer, hand-carried cardiac ultrasound (HCU) equipment, a smartphone, a laptop computer, a personal digital assistant (PDA), or a tablet personal computer (PC). The portable-type ultrasound diagnostic apparatus 200 may be, but is not limited to, an apparatus configured to only display an ultrasound image without separately performing image processing on ultrasound image data that is generated by the wireless ultrasound probe 100 and then is analog-to-digital converted.

The ultrasound diagnostic apparatus 200 may also include a battery as in the wireless ultrasound probe 100, may receive a charging power from the case 300 by using the wired charging method or the wireless charging method, and may charge the battery with the received charging power.

When a user pulls the wireless ultrasound probe 100 mounted in the case 300 out of the case 300, the wireless ultrasound probe 100 is detached from a charging terminal of the case 300. In this case, supply of the charging power from the case 300 is discontinued with respect to the wireless ultrasound probe 100.

The ultrasound diagnostic apparatus 200 may detect a state in which the wireless ultrasound probe 100 is detached from the case 300 and supply of the charging power from the case 300 is discontinued. In this case, the ultrasound diagnostic apparatus 200 performs wireless pairing with the wireless ultrasound probe 100 that has been detached from the charging terminal of the case 300. In this regard, the pairing may refer to a state of the ultrasound diagnostic apparatus 200 that is connected to the wireless ultrasound probe 100 in a wireless communication manner and receives, from the wireless ultrasound probe 100, probe characteristic information such as probe identification (ID) information, battery information, or the like. The term "pairing" and the term "activation" are different concepts, and will be described below with reference to FIG. 5.

The ultrasound diagnostic apparatus 200 may be paired with the wireless ultrasound probe 100 by using at least one of data communication schemes including wireless local area network (LAN), WiFi, Bluetooth, Zigbee, WiFi Direct (WFD), infrared Data Association (IrDA), Bluetooth Low Energy (BLE), near-field communication (NFC), Wireless Broadband Internet (WiBro), Worldwide Interoperability for Microwave Access (WiMAX), Shared Wireless Access Protocol (SWAP), Wireless Gigabit Alliance (WiGig) and radio frequency communication (RF communication).

When the wireless ultrasound probe 100 is paired with the ultrasound diagnostic apparatus 200, the wireless ultrasound probe 100 may transmit, to the ultrasound diagnostic apparatus 200, probe characteristic information including at least one of ID information, a wireless ultrasound probe's type, a radio frequency range of use, depth value information, and remaining battery amount information. The ultrasound diagnostic apparatus 200 may load a preset UI for an ultrasound diagnosis, based on the probe characteristic information and system information which are received from the wireless ultrasound probe 100, and may display the loaded preset UI on a display 230.

The preset UI displayed on the display 230 may be a UI that indicates probe characteristic information including at least one of ID information such as a model name (e.g., L3-12W) of the paired wireless ultrasound probe 100, a wireless communication scheme (e.g., WiFi) enabling pairing between the wireless ultrasound probe 100 and the ultrasound diagnostic apparatus 200, a wireless communication scheme (e.g., a short-range wireless communication scheme of 60 GHz) enabling transmitting and receiving ultrasound data, a remaining battery amount of the wireless ultrasound probe 100, depth value information, and a radio frequency range of use. The preset UI may be a graphical user interface (GUI) that indicates the probe characteristic information of the wireless ultrasound probe 100.

Referring to FIG. 1B, the wireless ultrasound probe 100 may receive a charging power for charging a battery from a charging terminal 211 of an ultrasound diagnostic apparatus 201.

The ultrasound diagnostic apparatus 201 may be a cart-type ultrasound diagnostic apparatus and may be a system for generating ultrasound raw data from an ultrasound echo signal obtained from the wireless ultrasound probe 100, and for generating an ultrasound image by performing analog-to-digital conversion on the ultrasound raw data. The ultrasound diagnostic apparatus 201 may supply the charging power to the wireless ultrasound probe 100 attached to the charging terminal 211.

The ultrasound diagnostic apparatus 201 may detect a state in which the wireless ultrasound probe 100 is detached from the charging terminal 211 and supply of the charging power is discontinued. In this case, the ultrasound diagnostic apparatus 201 performs wireless pairing with the wireless ultrasound probe 100 that has been detached from the charging terminal 211. Descriptions about the pairing are the same as that of FIG. 1A, therefore, redundant descriptions thereof are not provided here.

When the wireless ultrasound probe 100 is paired with the ultrasound diagnostic apparatus 201, the wireless ultrasound probe 100 may transmit, to the ultrasound diagnostic apparatus 201, probe characteristic information including at least one of ID information, a wireless ultrasound probe's type, a radio frequency range of use, depth value information, and remaining battery amount information. The ultrasound diagnostic apparatus 201 may load a preset UI for an ultrasound diagnosis, based on the received probe characteristic information, and may display the loaded preset UI on a display 231.

The preset UI displayed on the display 231 is the same as the present UI displayed on the display 230 described with reference to FIG. 1A, therefore, redundant descriptions thereof are not provided here.

According to a method of pairing ultrasound diagnostic apparatus and a wireless ultrasound probe according to the related art, a user has to select a wireless ultrasound probe to be used in examining an object and to make a separate input such as a direct button input, a touch input with respect to a touchscreen, or the like to allow the wireless ultrasound probe to transmit a pairing signal to the ultrasound diagnostic apparatus.

The embodiment illustrated in FIGS. 1A and 1B provides the ultrasound diagnostic apparatus 200 or 201 that may detect a state in which the wireless ultrasound probe 100 is detached from a charging terminal and supply of a charging power for charging a battery of the wireless ultrasound probe 100 is discontinued, and may be automatically paired with the wireless ultrasound probe 100 for which supply of the charging power is discontinued. Therefore, when a user wants to use the wireless ultrasound probe 100, the ultrasound diagnostic apparatus 200 or 201 according to the embodiment may make the user immediately use the wireless ultrasound probe 100 without a separate pairing process with respect to the wireless ultrasound probe 100, and thus may improve user convenience. In addition, the ultrasound diagnostic apparatus 200 or 201 may display a UI indicating probe characteristic information including a connection state of the paired wireless ultrasound probe 100, and may display a related preset UI based on the probe characteristic information so as to examine an object by immediately transmitting an ultrasound signal thereto, such that a waste of time due to a setting for examination may be reduced, and usability may be significantly improved.

Figure 2:
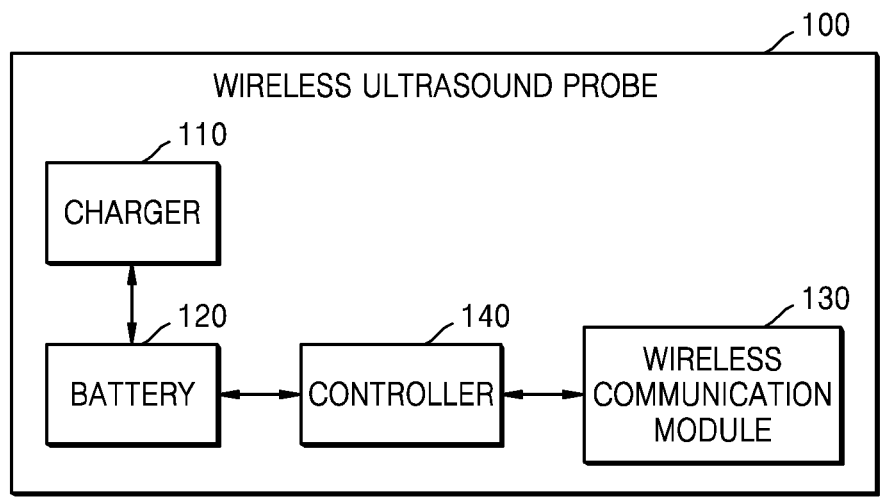
FIG. 2 is a block diagram illustrating a configuration of the wireless ultrasound probe according to an embodiment.

FIG. 2 is a block diagram illustrating a configuration of the wireless ultrasound probe 100 according to an embodiment.

Referring to FIG. 2, the wireless ultrasound probe 100 may include a charger 110, a battery 120, a wireless communication module 130, and a controller 140. The charger 110 may charge the battery 120 by receiving power from a charging power supplier 210 (refer to FIG. 3) of the ultrasound diagnostic apparatus 200. The charger 110 may be formed to have a unique shape to be physically attached to the charging terminal 211 (refer to FIG. 1B) of the ultrasound diagnostic apparatus 201.

The charger 110 may charge the battery 120 by receiving power from a charging power supplier 320 (refer to FIG. 4) of the case 300. In this case, the charger 110 may receive a charging power from the charging power supplier 320 of the case 300 in a wired manner by using a cable or by using a wireless charging method using at least one a wireless charging pad or a wireless charging coil.

The battery 120 may supply an operating power to the wireless ultrasound probe 100. In particular, the battery 120 may supply the operating power to the wireless communication module 130 and the controller 140. In this regard, the operating power may refer to power that is generated by the battery 120 and is supplied to allow the wireless communication module 130 and the controller 140 to perform respective functions. The battery 120 may be a rechargeable secondary battery. The battery 120 may be, but is not limited to, a lithium-ion (Li-ion) battery. For example, the battery 120 may be configured as a Li-ion battery, a Li polymer battery, a nickel-cadmium (Ni—Cd) battery, a lead storage battery, or a nickel metal hydride (NiMH) battery.

The wireless communication module 130 may perform pairing with an ultrasound diagnostic apparatus by using a wireless communication scheme. For example, the wireless communication module 130 may be wirelessly paired with the ultrasound diagnostic apparatus by using at least one of data communication schemes including LAN, WiFi, Bluetooth, Zigbee, WFD, IrDA, BLE, NFC, WiBro, WiMAX, SWAP, WiGig and a RF communication scheme.

In the present embodiment, the wireless communication module 130 may include a 60 GHz millimeter (mm) wave data communication module configured to transmit ultrasound raw data to the ultrasound diagnostic apparatus. In another embodiment, the wireless communication module 130 may include only a short-range communication module for pairing with the ultrasound diagnostic apparatus.

The controller 140 may detect a detachment signal with which the charger 110 is detached from the charging power supplier 210 (refer to FIG. 3) of the ultrasound diagnostic apparatus 200. The controller 140 may detect a state in which supply of the charging power is discontinued, and may control the wireless communication module 130 to be wirelessly paired with the ultrasound diagnostic apparatus. The controller 140 may detect a charging-discontinued state, and, in the charging-discontinued state, the controller 140 may control the wireless communication module 130 to be wirelessly paired with the ultrasound diagnostic apparatus.

After being paired with the ultrasound diagnostic apparatus, the controller 140 may control the wireless communication module 130 to transmit, to the ultrasound diagnostic apparatus, probe characteristic information including at least one of ID information of the wireless ultrasound probe 100, a type of the wireless ultrasound probe 100, a radio frequency range of use, depth value information, and remaining battery amount information. In this regard, the ID information of the wireless ultrasound probe 100 may refer to model name information of the wireless ultrasound probe 100, and the type may refer to information indicating a convex probe type or a linear probe type.

After the wireless ultrasound probe 100 is paired with the ultrasound diagnostic apparatus, the controller 140 may automatically perform beamforming to transmit an ultrasound signal to an object, based on a preset activation signal. For example, the controller 140 may detect an activation signal indicating at least one of contact between the wireless ultrasound probe 100 and the object, application of a gel with respect to the wireless ultrasound probe 100, motion of a user holding the wireless ultrasound probe 100, and a button input for transmitting an ultrasound signal, and may automatically perform beamforming, in response to the activation signal.

The controller 140 may detect a state in which supply of the charging power from the case 300 (refer to FIG. 4) to the wireless ultrasound probe 100 is discontinued, and may control the wireless communication module 130 to be wirelessly paired with the ultrasound diagnostic apparatus, in the state in which supply of the charging power from the case 300 is discontinued.

Figure 3:
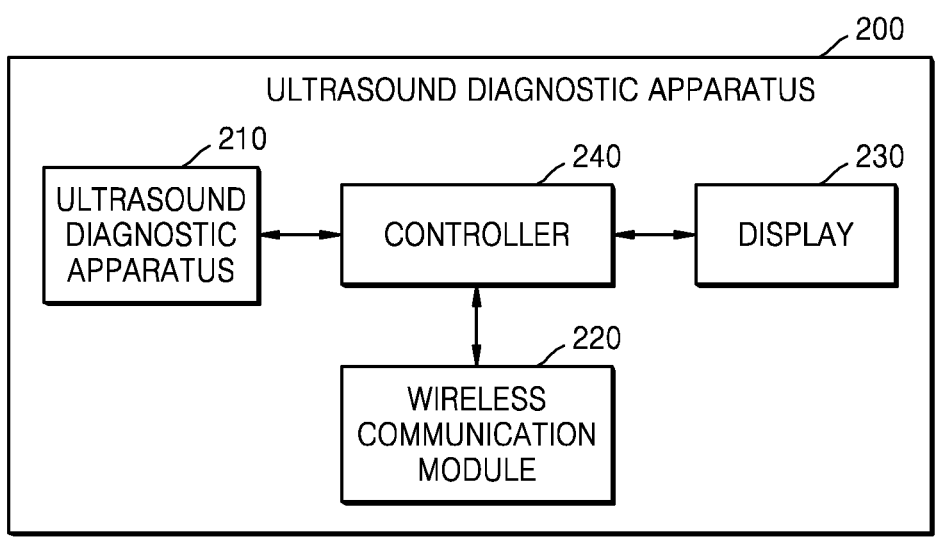
FIG. 3 is a block diagram illustrating a configuration of the ultrasound diagnostic apparatus according to an embodiment.

FIG. 3 is a block diagram illustrating a configuration of the ultrasound diagnostic apparatus 200 according to an embodiment.

The ultrasound diagnostic apparatus 200 may be wirelessly connected to a wireless ultrasound probe. The ultrasound diagnostic apparatus 200 may be embodied as a cart-type ultrasound diagnostic apparatus or a portable-type ultrasound diagnostic apparatus. For example, the portable-type ultrasound diagnostic apparatus may include, but is not limited to, a PACS viewer, HCU equipment, a smartphone, a laptop computer, a PDA, or a tablet PC.

In an embodiment, the ultrasound diagnostic apparatus 200 may be an apparatus configured to generate an ultrasound image by processing ultrasound image data received from a wireless ultrasound probe and to display the generated ultrasound image, or may be an apparatus configured to only display an ultrasound image without separately performing image processing.

Referring to FIG. 3, the ultrasound diagnostic apparatus 200 may include a charging power supplier 210, a wireless communication module 220, a display 230, and a controller 240. The charging power supplier 210 may charge a battery (refer to the battery 120 of FIG. 2) of a wireless ultrasound probe by supplying power to the wireless ultrasound probe. The charging power supplier 210 may be physically attached to a charger (refer to the charger 110 of FIG. 2) of the wireless ultrasound probe. In an embodiment, the charging power supplier 210 may include a charging terminal having a unique shape to be attached to only the wireless ultrasound probe including the charger (refer to the charger 110 of FIG. 2) having a preset shape.

The wireless communication module 220 may be connected to the wireless ultrasound probe by using a wireless communication scheme. For example, the wireless communication module 220 may be wirelessly paired with the wireless ultrasound probe by using at least one of wireless communication schemes including LAN, WiFi, Bluetooth, Zigbee, WFD, IrDA, BLE, NFC, WiBro, WiMAX, SWAP, WiGig and a RF communication scheme.

The display 230 may display a UI indicating probe characteristic information of the paired wireless ultrasound probe. In an embodiment, the display 230 may display a UI indicating probe characteristic information including at least one of ID information of the paired wireless ultrasound probe, a type of the wireless ultrasound probe, a radio frequency range of use, depth value information, and remaining battery amount information.

The display 230 may be formed as a physical device including, but is not limited to, at least one of a liquid crystal display (LCD) display, a plasma display panel (PDP) display, an organic light-emitting diode (OLED) display, a field-emission display (FED) display, a light-emitting diode (LED) display, a vacuum fluorescent display (VFD) display, a Digital Light Processing (DLP) display, a flat panel display, a three-dimensional (3D) display, and a transparent display. In an embodiment, the display 230 may be formed as a touchscreen including a touch interface.

The controller 240 may detect a detachment signal with which the wireless ultrasound probe that has been being charged is detached from the charging power supplier 210. In response to the detachment signal, the controller 240 may control the wireless communication module 220 to be paired by using a wireless communication scheme with the wireless ultrasound probe for which supply of a charging power is discontinued.

When supply of the charging power is discontinued, the controller 240 may control the wireless communication module 220 to receive, from the paired wireless ultrasound probe, the probe characteristic information including at least one of the ID information of the paired wireless ultrasound probe, the type of the wireless ultrasound probe, the radio frequency range of use, the depth value information, and the remaining battery amount information.

The controller 240 may generate a beamforming control signal for transmitting an ultrasound signal to an object, in response to an activation signal detected by the paired wireless ultrasound probe. The activation signal may indicate at least one of contact between the wireless ultrasound probe and the object, application of a gel with respect to the wireless ultrasound probe, motion of a user holding the wireless ultrasound probe, and a button input for transmitting an ultrasound signal. The controller 240 may control the wireless communication module 220 to transmit, to the wireless ultrasound probe, the beamforming control signal generated in response to the activation signal.

The wireless ultrasound probe and the ultrasound diagnostic apparatus 200 may be placed in a case (refer to the case 300 of FIGS. 1 and 4), and the wireless ultrasound probe may receive a charging power for charging the battery from the case 300. In this case, the controller 240 may detect a detachment signal with which the wireless ultrasound probe is detached from the case 300, and may control the wireless communication module 220 to be wirelessly paired with the wireless ultrasound probe.

The controller 240 may be a hardware module including at least one of a central processing unit (CPU), a microprocessor, a graphics processing unit (GPU), a random-access memory (RAM), and a read-only memory (ROM). In a case where the ultrasound diagnostic apparatus 200 is a portable-type ultrasound diagnostic apparatus including a smartphone, a laptop computer, a PDA, a tablet PC, or the like, the controller 240 may be configured as an application processor (AP).

The ultrasound diagnostic apparatus 200 may further include a memory (not shown). The memory may store system information for obtain an ultrasound image according to ID information and a type of the wireless ultrasound probe, and the preset UI which is UI pattern according to a format of the ultrasound image. The controller 240 may load, from the memory, the preset UI, based on the ID information and the type of the wireless ultrasound probe which is included in the received probe characteristic information, and may display the loaded preset UI on the display 230.

Figure 4:
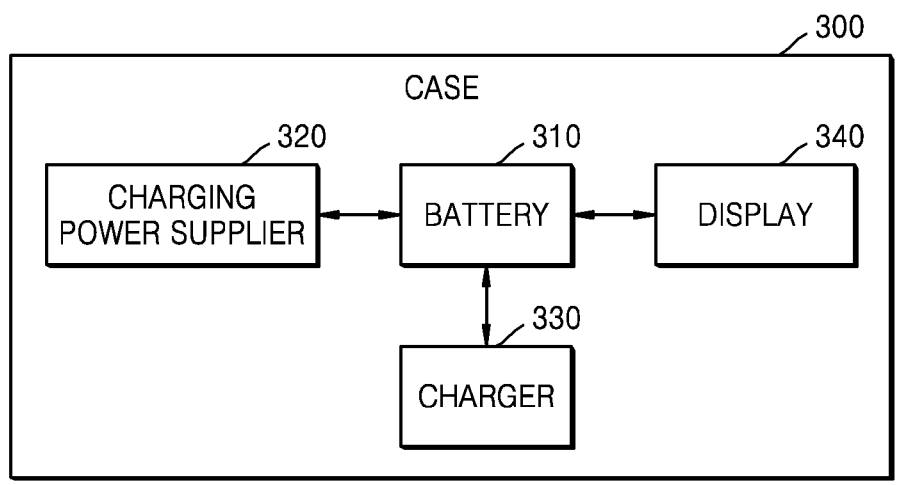
FIG. 4 is a block diagram illustrating a configuration of a case according to an embodiment.

FIG. 4 is a block diagram illustrating a configuration of the case 300 according to an embodiment. The case 300 may store a wireless ultrasound probe and an ultrasound diagnostic apparatus, and may supply a charging power to the wireless ultrasound probe and the ultrasound diagnostic apparatus stored in the case 300. In this regard, charging is performed only when the wireless ultrasound probe and the ultrasound diagnostic apparatus are stored in the case 300, and when the wireless ultrasound probe and the ultrasound diagnostic apparatus are detached from the case 300 and are carried out, charging is discontinued.

Referring to FIG. 4, the case 300 may include a battery 310, a charging power supplier 320, a charger 330, and a display 340. The battery 310 may be embedded in the case 300 and may supply a charging power to the wireless ultrasound probe and the ultrasound diagnostic apparatus via the charging power supplier 320. The battery 310 may be a rechargeable secondary battery. The battery 310 may include, but is not limited to, a Li-ion battery. For example, the battery 310 may be configured as a Li-ion battery, a Li polymer battery, a Ni—Cd battery, a lead storage battery, or a NiMH battery.

The charging power supplier 320 may charge a battery (refer to the battery 120 of FIG. 2) of the wireless ultrasound probe by supplying power to the wireless ultrasound probe. In an embodiment, in a case where the ultrasound diagnostic apparatus is embodied as a portable-type ultrasound diagnostic apparatus and has a battery embedded therein, the charging power supplier 320 may also supply a charging power to the portable-type ultrasound diagnostic apparatus. In this case, the charging power supplier 320 may include a first charger and a second charger, the first charger being configured to supply a charging power to the wireless ultrasound probe and the second charger being configured to supply a charging power to the ultrasound diagnostic apparatus.

The charging power supplier 320 may supply a charging power to the wireless ultrasound probe in a wired manner using a cable, but is not limited thereto. In an embodiment, the charging power supplier 320 may supply a charging power to the wireless ultrasound probe by using a wireless charging method using a wireless charging pad, a wireless charging coil, or the like.

The charger 330 charges the battery 310 by receiving power from an external source. For example, the charger 330 may charge the battery 310 by receiving power via a wall power supply.

The display 340 may display a UI indicating a remaining amount of each of batteries respectively embedded in the wireless ultrasound probe and the ultrasound diagnostic apparatus. In an embodiment, the display 340 may display a UI displaying a remaining amount of the battery 310. The display 340 may display respective thumbnail images of the wireless ultrasound probe, the ultrasound diagnostic apparatus, and the case 300, and may display GUIs respectively indicating remaining battery amounts of the wireless ultrasound probe, the ultrasound diagnostic apparatus, and the case 300 at respective positions above the thumbnail images. This will be described below with reference to FIG. 8.

Figure 5:
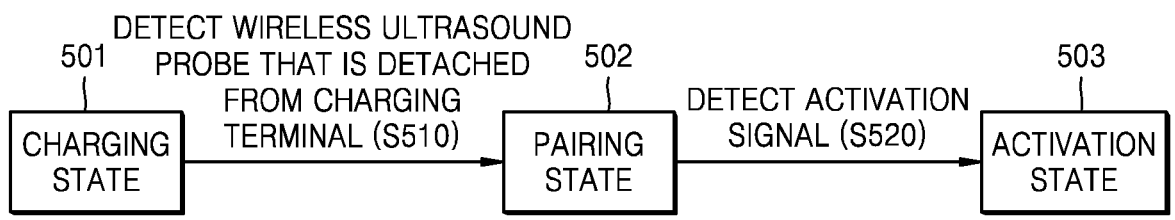
FIG. 5 is a flowchart illustrating an operating method of an ultrasound diagnostic apparatus based on a state of the ultrasound diagnostic apparatus, according to an embodiment.

FIG. 5 is a flowchart illustrating an operating method of an ultrasound diagnostic apparatus based on a state of the ultrasound diagnostic apparatus, according to an embodiment.

Referring to FIG. 5, a charging state 501 refers to a state in which the ultrasound diagnostic apparatus supplies a charging power to a wireless ultrasound probe and charges a battery embedded in the wireless ultrasound probe. A charger to be physically attached to a charging terminal of the ultrasound diagnostic apparatus may be arranged in the wireless ultrasound probe, and the wireless ultrasound probe may receive a charging power from the ultrasound diagnostic apparatus via the charger.

In operation S510, the ultrasound diagnostic apparatus detects the wireless ultrasound probe that is detached from the charging terminal. In operation S510, the ultrasound diagnostic apparatus may detect a state where the wireless ultrasound probe is physically detached from the charging terminal, and a state where supply of a charging power is discontinued.

A pairing state 502 refers to a state in which the ultrasound diagnostic apparatus is connected to the wireless ultrasound probe by using a wireless communication method. In this regard, pairing may refer to a state in which the ultrasound diagnostic apparatus is connected to the wireless ultrasound probe by using the wireless communication method and then receives probe characteristic information including probe ID information, battery information, or the like from the wireless ultrasound probe. In the pairing state 502, the ultrasound diagnostic apparatus may detect, as an event signal, a signal with which the wireless ultrasound probe is detached from the charging terminal, and may be paired with the wireless ultrasound probe in response to the event signal, the wireless ultrasound probe having been detached from the charging terminal.

In the pairing state 502, the ultrasound diagnostic apparatus may be paired with the wireless ultrasound probe by using at least one of data communication schemes including LAN, WiFi, Bluetooth, Zigbee, WFD, IrDA, BLE, NFC, WiBro, WiMAX, SWAP, WiGig and RF communication.

In operation S520, the ultrasound diagnostic apparatus detects an activation signal. In the pairing state 502, the ultrasound diagnostic apparatus may detect various signals or the activation signal including a user input which are detected via the wireless ultrasound probe. In an embodiment, the ultrasound diagnostic apparatus may detect the activation signal indicating at least one of contact between the wireless ultrasound probe and an object, application of a gel with respect to the wireless ultrasound probe, motion of a user holding the wireless ultrasound probe, and a button input for transmitting an ultrasound signal.

An activation state 503 refers to a state in which the ultrasound diagnostic apparatus is ready to transmit an ultrasound signal to an object, based on probe ID information and a probe type which are received from the paired wireless ultrasound probe, i.e., an ultrasound transmission-ready state. In the activation state 503, the ultrasound diagnostic apparatus may receive, from the wireless ultrasound probe, probe characteristic information including at least one of probe ID information, a probe type, a radio frequency range of use, depth value information, and remaining battery amount information, and may load and download a preset to a field-programmable gate array (FPGA), the preset being for transmitting an ultrasound wave to the object, based on the received probe characteristic information. In the activation state 503, the ultrasound diagnostic apparatus may transmit a beamforming control signal to the wireless ultrasound probe, based on the loaded preset.

Figure 6:
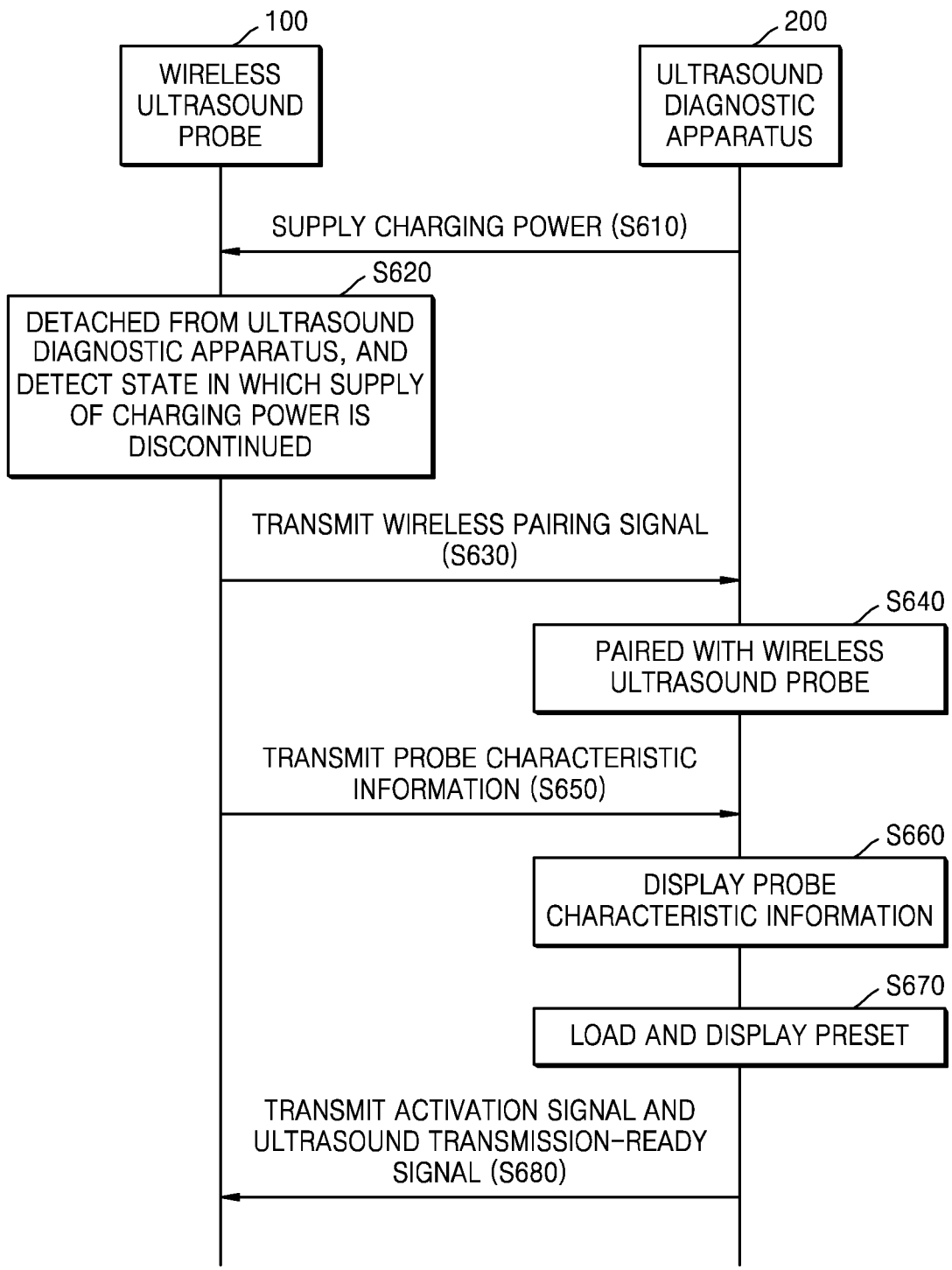
FIG. 6 is a flowchart illustrating an operating method performed between the wireless ultrasound probe and the ultrasound diagnostic apparatus, according to an embodiment.

FIG. 6 is a flowchart illustrating an operating method performed between the wireless ultrasound probe 100 and the ultrasound diagnostic apparatus 200, according to an embodiment.

In operation S610, the ultrasound diagnostic apparatus 200 supplies a charging power to the wireless ultrasound probe 100. Operation S610 may correspond to a charging state, and in the charging state, the ultrasound diagnostic apparatus 200 may supply a charging power to the wireless ultrasound probe 100 attached to the charging terminal and may charge the battery 120 embedded in the wireless ultrasound probe 100.

In operation S620, the wireless ultrasound probe 100 is detached from the ultrasound diagnostic apparatus 200 and detects a state in which supply of the charging power is discontinued. The wireless ultrasound probe 100 may detect a state in which the wireless ultrasound probe 100 is physically detached from the charging terminal of the ultrasound diagnostic apparatus 200, and a state in which supply of the charging power from the ultrasound diagnostic apparatus 200 is discontinued.

In operation S630, the wireless ultrasound probe 100 transmits a wireless pairing signal to the ultrasound diagnostic apparatus 200, and in operation S640, the ultrasound diagnostic apparatus 200 is wirelessly paired with the wireless ultrasound probe 100. In operations S630 and S640, the wireless pairing signal may be exchanged between the wireless ultrasound probe 100 and the ultrasound diagnostic apparatus 200 by using at least one of data communication schemes including LAN, WiFi, Bluetooth, Zigbee, WFD, IrDA, BLE, NFC, WiBro, WiMAX, SWAP, WiGig and RF communication, and the wireless ultrasound probe 100 and the ultrasound diagnostic apparatus 200 may be paired with each other by using at least one of the data communication schemes.

In operation S650, the wireless ultrasound probe 100 transmits probe characteristic information to the ultrasound diagnostic apparatus 200. The probe characteristic information may include at least one of ID information of the wireless ultrasound probe 100, a type of the wireless ultrasound probe 100, a radio frequency range of use, depth value information, and remaining battery amount information. In this regard, the ID information of the wireless ultrasound probe 100 may refer to model name information of the wireless ultrasound probe 100, and the type may refer to information indicating a convex probe type or a linear probe type.

In operation S660, the ultrasound diagnostic apparatus 200 displays the probe characteristic information. In an embodiment, the ultrasound diagnostic apparatus 200 may include the display 230, and the ultrasound diagnostic apparatus 200 may display, on the display 230, a UI that indicates, by using a text or an icon, the probe characteristic information received from the wireless ultrasound probe 100 in operation S650.

In operation S670, the ultrasound diagnostic apparatus 200 loads a preset stored in a memory, and displays the loaded preset. In an embodiment, the ultrasound diagnostic apparatus 200 may include the memory, and the memory may store the probe characteristic information, system information, and the preset including UI pattern information about formats of ultrasound images. The ultrasound diagnostic apparatus 200 may load the preset, based on the probe characteristic information received from the wireless ultrasound probe 100 in operation S650. For example, the ultrasound diagnostic apparatus 200 may load, from the memory, system information for obtaining an ultrasound image and a preset of a UI pattern about a format (a convex image or a linear image) of the ultrasound image, based on the ID information and the type of the wireless ultrasound probe 100 which are included in the received probe characteristic information. The ultrasound diagnostic apparatus 200 may display, on the display 230, the UI pattern and the format of the ultrasound image, based on the loaded preset. This will be described below with reference to FIGS. 9A and 9B.

In operation S680, the ultrasound diagnostic apparatus 200 transmits an activation signal and an ultrasound transmission-ready signal to the wireless ultrasound probe 100. In an embodiment, the ultrasound diagnostic apparatus 200 may transmit a beamforming control signal to the wireless ultrasound probe 100 so as to allow the paired wireless ultrasound probe 100 to transmit an ultrasound signal to an object. In this case, the wireless ultrasound probe 100 may be an ultrasound probe that autonomously includes a beamformer, and the ultrasound diagnostic apparatus 200 may transmit the beamforming control signal to the wireless ultrasound probe 100 by using a wireless communication method, the beamforming control signal being used to control the beamformer in the wireless ultrasound probe 100 to transmit the ultrasound signal to the object. The wireless ultrasound probe 100 may be activated in response to the beamforming control signal, and may be switched to an activation state that is a state in which the wireless ultrasound probe 100 is ready to transmit the ultrasound signal to the object.

Figure 7:
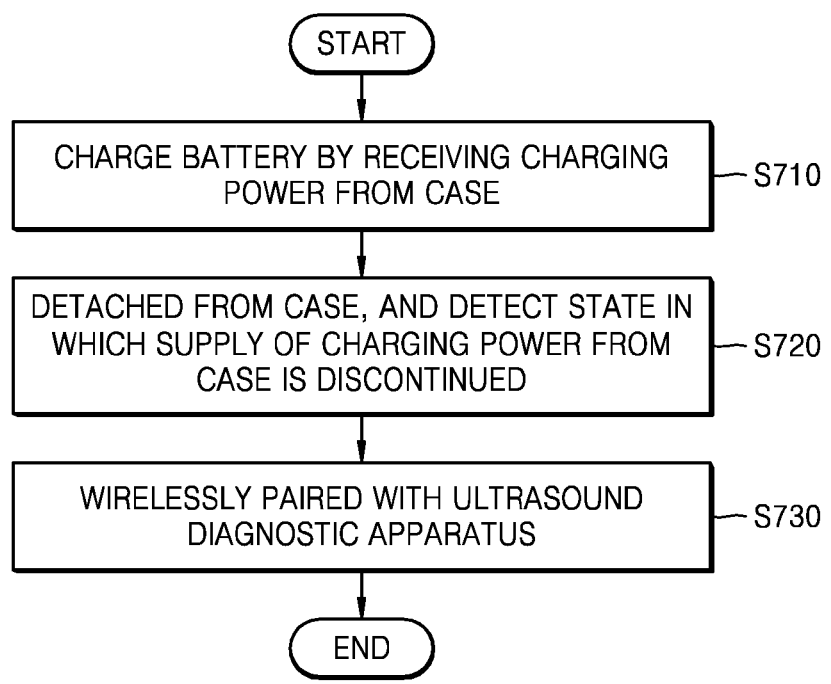
FIG. 7 is a flowchart illustrating an operating method of a wireless ultrasound probe, according to an embodiment.

FIG. 7 is a flowchart illustrating an operating method of a wireless ultrasound probe, according to an embodiment.

In operation S710, an ultrasound diagnostic apparatus charges an embedded battery by receiving a charging power from a case. The wireless ultrasound probe may charge its battery by receiving the charging power from the case by using a wired charging method using a cable or by using a wireless charging method using a wireless charging pad, a wireless charging coil, or the like.

In an embodiment, not only the wireless ultrasound probe but also the ultrasound diagnostic apparatus may be arranged in the case and may receive the charging power from the case. In this case, the ultrasound diagnostic apparatus may be a portable-type ultrasound diagnostic apparatus including a battery. The portable-type ultrasound diagnostic apparatus may be an apparatus configured to only display an ultrasound image without separately performing image processing on ultrasound image data that is generated by the wireless ultrasound probe and then is analog-to-digital converted.

In operation S720, the wireless ultrasound probe is detached from the case and detects a state in which supply of the charging power from the case is discontinued. In an embodiment, when a user pulls the wireless ultrasound probe out of the case, the wireless ultrasound probe may detect a signal with which the wireless ultrasound probe is physically detached from a charging terminal of the case or the wireless charging pad, and may detect that supply of the charging power from the case is discontinued. In an embodiment, the wireless ultrasound probe may detect the signal involving detachment from the case, as an event signal for pairing.

In operation S730, the wireless ultrasound probe is paired with the ultrasound diagnostic apparatus by using a wireless communication method. Descriptions about the pairing are same as those described with reference to the pairing state 502 of FIG. 5 and operation S640 of FIG. 6, therefore, redundant descriptions are not provided here.

Figure 8:
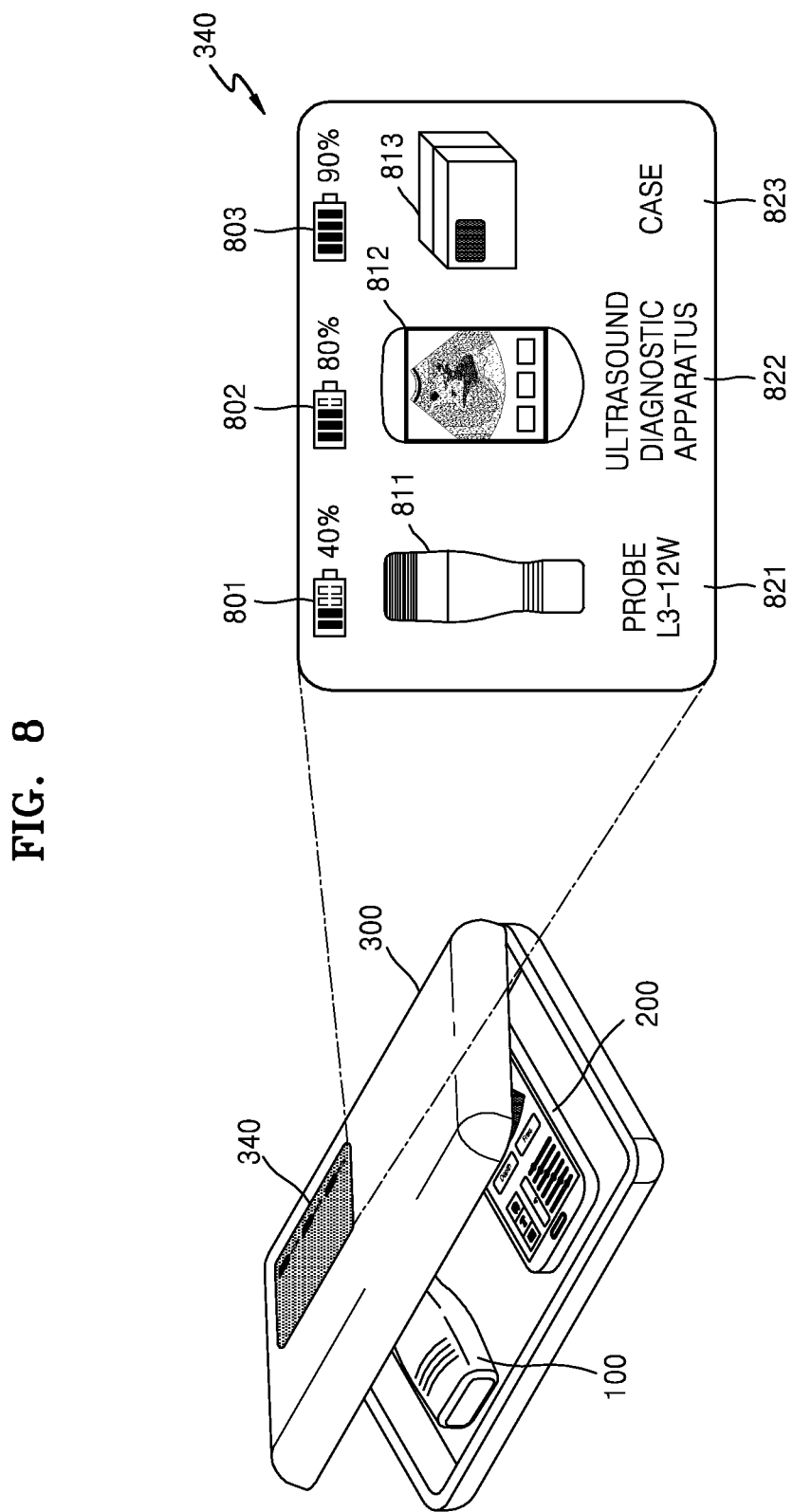
FIG. 8 is a diagram illustrating an embodiment in which the case displays battery state information of each of the wireless ultrasound probe, the ultrasound diagnostic apparatus, and the case.

FIG. 8 is a diagram illustrating an embodiment in which the case 300 displays battery state information of each of the wireless ultrasound probe 100, the ultrasound diagnostic apparatus 200, and the case 300.

Referring to FIG. 8, the case 300 may display, on the display 340, UIs 801 and 802 that indicate battery remaining amounts of the wireless ultrasound probe 100 and the ultrasound diagnostic apparatus 200 that are mounted in the case 300. In an embodiment, the display 340 may also display a UI 803 that indicates a remaining amount of the battery embedded in the case 300.

The display 340 may display respective thumbnail images 811, 812, and 813 of the wireless ultrasound probe 100, the ultrasound diagnostic apparatus 200, and the case 300, and may display UIs 801, 802, and 803 respectively indicating remaining amounts of the battery of the wireless ultrasound probe 100, the ultrasound diagnostic apparatus 200, and the case 300 at respective positions above the thumbnail images 811, 812, and 813. In an embodiment, the display 340 may display UIs 821, 822, and 823 which indicate, by using texts, respective ID information of the wireless ultrasound probe 100, the ultrasound diagnostic apparatus 200, and the case 300.

In a case where the wireless ultrasound probe 100 and the ultrasound diagnostic apparatus 200 that are embodied to be portable are mounted in the case 300 and receive a charging power from the case 300, it is difficult for a user to recognize a remaining battery amount of each of the wireless ultrasound probe 100 and the ultrasound diagnostic apparatus 200. According to the embodiment of FIG. 8, the display 340 of the case 300 displays not only respective remaining battery amounts of the wireless ultrasound probe 100 and the ultrasound diagnostic apparatus 200 but also displays a remaining amount of the battery embedded in the case 300, therefore, the user may check a remaining battery amount of each device at a glance and user convenience in a mobile environment may be improved.

Figure 9A:
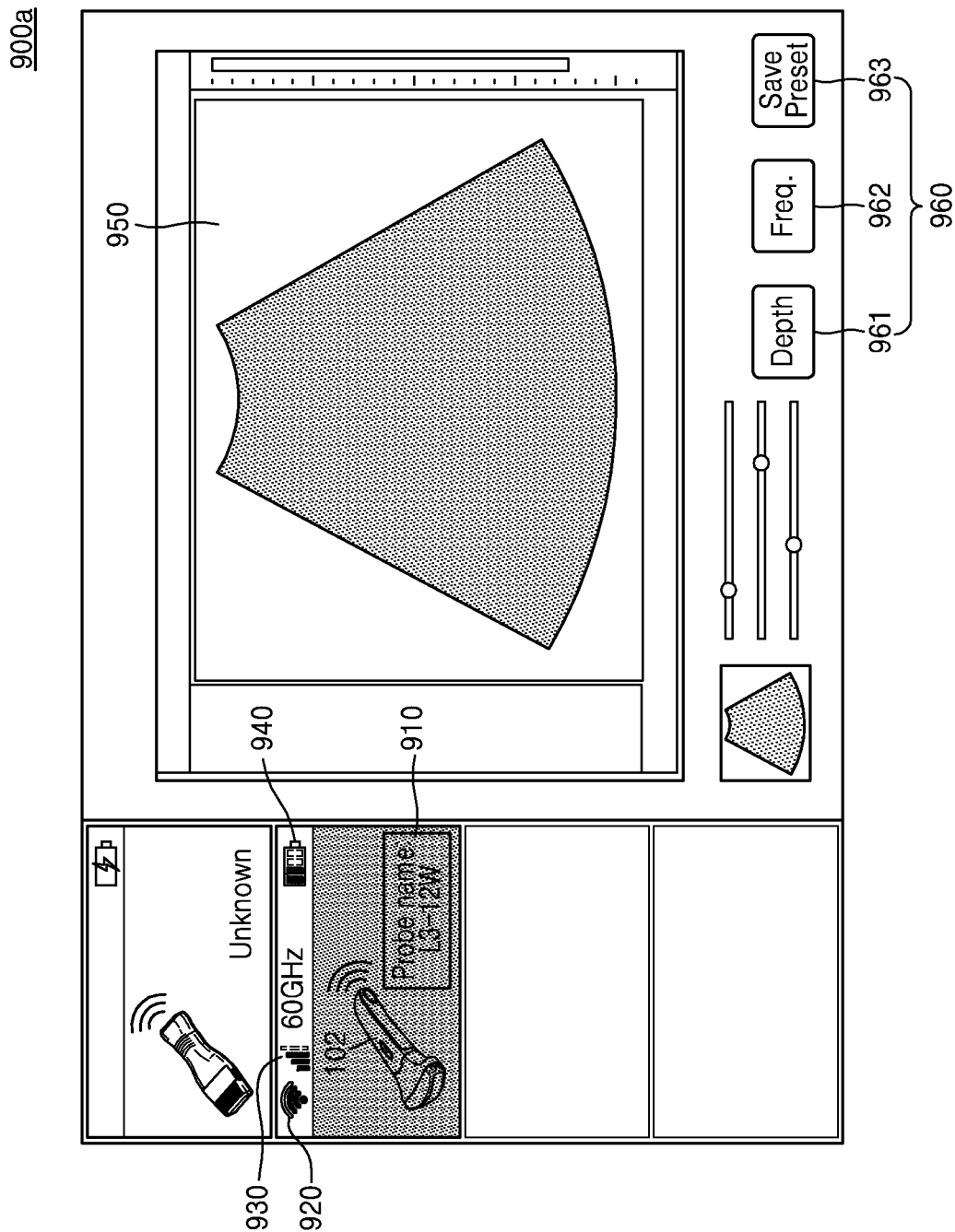
FIGS. 9A and 9B are diagrams illustrating embodiments in which an ultrasound diagnostic apparatus displays an activation-ready state, based on characteristic information of a wireless ultrasound probe.
Figure 9B:
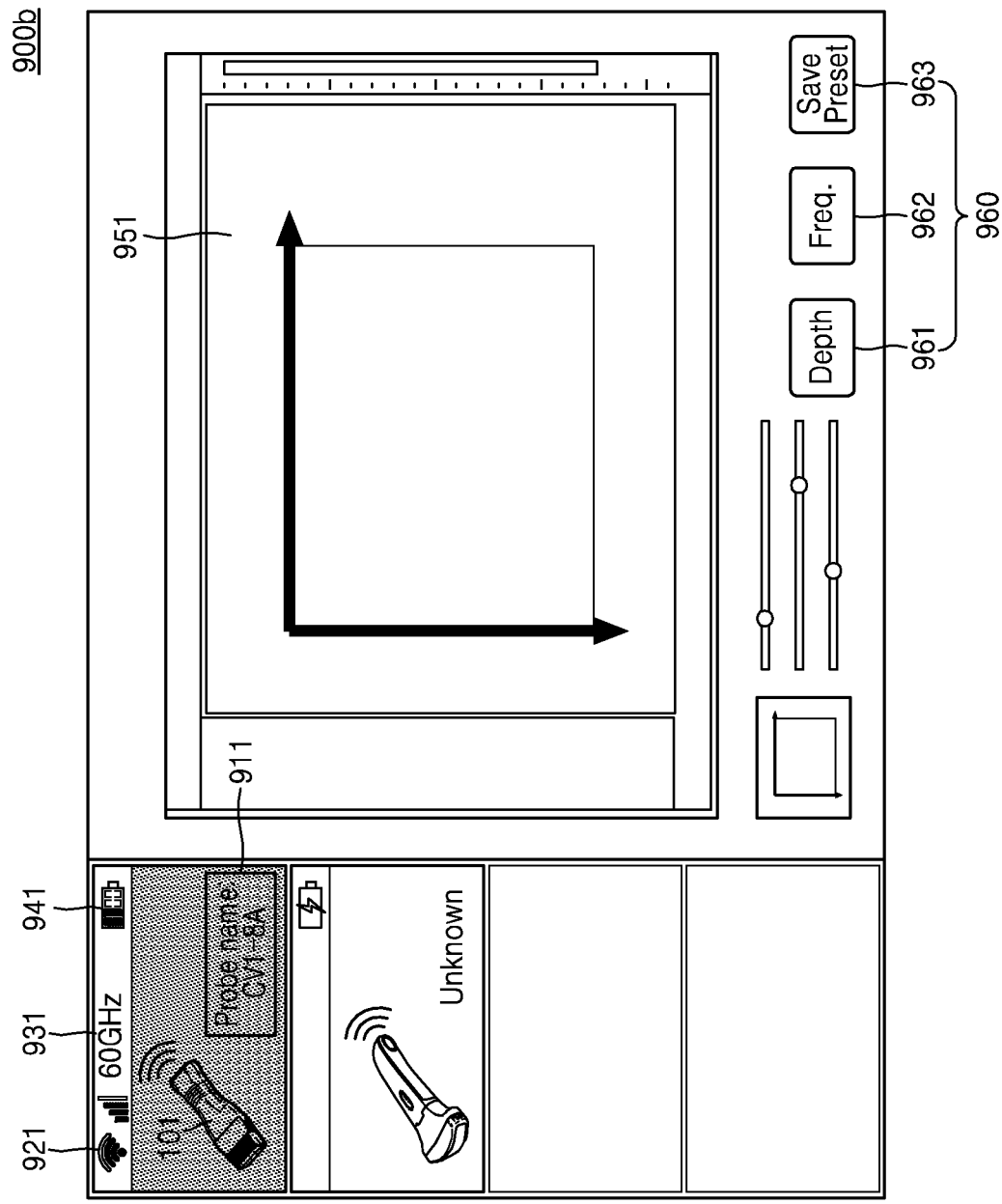

FIGS. 9A and 9B are diagrams illustrating embodiments in which an ultrasound diagnostic apparatus displays an activation-ready state, based on probe characteristic information of a wireless ultrasound probe.

Referring to FIG. 9A, a display 900a of an ultrasound diagnostic apparatus may display a UI including thumbnail images respectively showing shapes of a plurality of wireless ultrasound probes 101 and 102, and icons and texts indicating respective charging states and pairing states of the plurality of wireless ultrasound probes 101 and 102 (hereinafter, also referred to as the first and second wireless ultrasound probes 101 and 102). The display 900a may display preset UIs 950, 961, 962, and 963 that are loaded according to probe characteristic information of the second wireless ultrasound probe 102 that is paired with the ultrasound diagnostic apparatus and is from among the plurality of wireless ultrasound probes 101 and 102.

The display 900a may be an element of the ultrasound diagnostic apparatus, the element being provided on a control panel so as to display a UI, but is not limited thereto. The display 900a may display an ultrasound image generated by the wirelessly-paired second wireless ultrasound probe 102 from among the plurality of wireless ultrasound probes 101 and 102.

The UI including the thumbnail images of the plurality of wireless ultrasound probes 101 and 102 may be displayed on a side of the display 900a. Probe ID information is not displayed but 'Unknown' is displayed on the thumbnail image of the first wireless ultrasound probe 101, and an icon indicating charging is displayed on the thumbnail image of the first wireless ultrasound probe 101, this may mean that the first wireless ultrasound probe 101 that is not paired with the ultrasound diagnostic apparatus is being charged.

The display 900a may display a first UI 910 indicating ID information (e.g., L3-12W) of the second wireless ultrasound probe 102 on an area of the thumbnail image of the second wireless ultrasound probe 102, a second UI 920 indicating a wireless pairing scheme between the second wireless ultrasound probe 102 and the ultrasound diagnostic apparatus, a third UI 930 indicating a data communication scheme between the second wireless ultrasound probe 102 and the ultrasound diagnostic apparatus, and a fourth UI 940 indicating a remaining battery amount of the second wireless ultrasound probe 102. In this regard, the first UI 910 to the fourth UI 940 may be GUIs.

The first UI 910 indicating the ID information of the second wireless ultrasound probe 102 may be displayed using a text, but the second UI 920 and the third UI 930 that respectively indicate the wireless pairing scheme and the data communication scheme may be GUIs that indicate wireless connection states as the number of antennas. The second UI 920 may be a GUI of a symbol representing WiFi, Bluetooth, NFC, WiGig, or the like. In FIG. 9A, the number of antennas of the second UI 920 and the number of columns of the third UI 930 may be symbols visually indicating wireless connection states between the second wireless ultrasound probe 102 and the ultrasound diagnostic apparatus. For example, the higher the number of shaded-antennas in a fan-shaped antenna symbol in the second UI 920 indicating WiFi pairing, the better a WiFi pairing state between the second wireless ultrasound probe 102 and the ultrasound diagnostic apparatus may be.

In the embodiment of FIG. 9A, the second wireless ultrasound probe 102 may be wirelessly paired with the ultrasound diagnostic apparatus by using a WiFi communication scheme, and may perform data communication with the ultrasound diagnostic apparatus via 60 GHz mm wave short-range communication. In this regard, "pairing" and "data communication" are different concepts, where "pairing" may refer to a state in which a wireless ultrasound probe is connected to the ultrasound diagnostic apparatus by using a wireless communication scheme and transmits probe ID information, a probe type, battery information or the like. On the other hand, "data communication" may refer to wireless communication via which the wireless ultrasound probe transmits generated ultrasound raw data or analog-to-digital converted ultrasound image data to the ultrasound diagnostic apparatus.

In the embodiment of FIG. 9A, because the first wireless ultrasound probe 101 is not paired with the ultrasound diagnostic apparatus, the display 900a does not display any mark. However, because the second wireless ultrasound probe 102 is paired with the ultrasound diagnostic apparatus, the display 900a may display the area of the thumbnail image of the second wireless ultrasound probe 102 to be highlighted by using a different color or applying a shadow thereto. In an embodiment, the display 900a may perform bold lettering on a text indicating the ID information of the paired second wireless ultrasound probe 102.

A preset UI loaded according to the probe characteristic information of the paired second wireless ultrasound probe 102 may be displayed on a side of the display 900a. The preset UI may display a fifth UI 950 indicating an initial screen image of an ultrasound image, and a sixth UI 960 used in operations of the ultrasound diagnostic apparatus, the operations including an operation of obtaining an ultrasound image of an object, an operation of processing the obtained ultrasound image, or the like.

The fifth UI 950 indicates an initial screen image loaded based on a type of the paired second wireless ultrasound probe 102. In the embodiment of FIG. 9A, the second wireless ultrasound probe 102 may be a convex-type probe, and the fifth UI 950 may indicate an initial screen image for displaying a convex-type ultrasound image.

The sixth UI 960 displays UIs for changing a setting of the ultrasound diagnostic apparatus. For example, the sixth UI 960 may include a UI 961 for changing a setting of a depth value, a UI 962 for changing a frequency value, and a UI 963 for storing changed settings. In this regard, the sixth UI 960 is an example and the present disclosure is not limited to that shown in FIG. 9A.

Referring to FIG. 9B, a display 900b of an ultrasound diagnostic apparatus may display a UI including thumbnail images respectively showing shapes of the plurality of wireless ultrasound probes 101 and 102, and icons and texts indicating respective charging states and pairing states of the plurality of wireless ultrasound probes 101 and 102. The display 900b is equal to the display 900a of FIG. 9A, except that the display 900b is not paired with the second wireless ultrasound probe 102 but is paired with the first wireless ultrasound probe 101, and displays an initial screen image of a linear type in response to pairing with the first wireless ultrasound probe 101, therefore, redundant descriptions thereof are omitted.

In the embodiment of FIG. 9B, the UI including the thumbnail images of the plurality of wireless ultrasound probes 101 and 102 may be displayed on a side of the display 900b. A first UI 911 indicating probe ID information (e.g., CV1-8A) by using a text, a second UI 921 indicating a wireless pairing scheme between the first wireless ultrasound probe 101 and the ultrasound diagnostic apparatus, a third UI 931 indicating a data communication scheme between the first wireless ultrasound probe 101 and the ultrasound diagnostic apparatus, and a fourth UI 941 indicating a remaining battery amount of the first wireless ultrasound probe 101 may be displayed on an area of the thumbnail image of the first wireless ultrasound probe 101.

In the embodiment of FIG. 9B, the first wireless ultrasound probe 101 may be wirelessly paired with the ultrasound diagnostic apparatus by using a WiFi communication scheme, and may perform data communication with the ultrasound diagnostic apparatus via 60 GHz mm wave short-range communication. Thus, the display 900b may display the second UI 921 that is a GUI indicating WiFi, and the third UI 931 that is a GUI indicating a 60 GHz mm wave short-range communication scheme.

On the other hand, a text 'Unknown' may be displayed on an area of the thumbnail image of the second wireless ultrasound probe 102, and an icon indicating charging may be displayed on the thumbnail image of the second wireless ultrasound probe 102. This may mean that the second wireless ultrasound probe 102 that is not paired with the ultrasound diagnostic apparatus is being charged.

In the embodiment of FIG. 9B, the display 900b may display the area of the thumbnail image of the first wireless ultrasound probe 101 to be highlighted by using a different color or applying a shadow thereto, the first wireless ultrasound probe 101 being paired with the ultrasound diagnostic apparatus. However, the display 900b may not display a mark on the second wireless ultrasound probe 102 that is not paired and is only being charged.

Preset UIs 951, 961, 962, and 963 that are loaded according to probe characteristic information of the first wireless ultrasound probe 101 that is paired with the ultrasound diagnostic apparatus may be displayed on a side of the display 900b. The preset UI includes a fifth UI 951 indicating an initial screen image of an ultrasound image, and a sixth UI 960 being used in operations of the ultrasound diagnostic apparatus, the operations including an operation of obtaining an ultrasound image of an object, an operation of processing the obtained ultrasound image, or the like.

The fifth UI 951 indicates an initial screen image loaded based on a type of a paired wireless ultrasound probe. In the embodiment of FIG. 9B, the first wireless ultrasound probe 101 may be a linear-type probe, and the fifth UI 951 may indicate an initial screen image for displaying a linear-type ultrasound image.

According to the embodiments of FIGS. 9A and 9B, the displays 900a and 900b according to the present disclosure may display probe characteristic information including ID information of a wireless ultrasound probe paired with an ultrasound diagnostic apparatus, a pairing method, a data communication scheme, remaining battery amount information, or the like, and may display a preset UI indicating an initial screen image for displaying an ultrasound image, according to a type of the paired wireless ultrasound probe. Before an ultrasound signal is directly transmitted to an object, the displays 900a and 900b may automatically display a convex-type initial screen image or a linear-type initial screen image according to a type of a wireless ultrasound probe to be used by the user, therefore, the user does not have to additional manipulation and user convenience may be improved.

Figure 10:
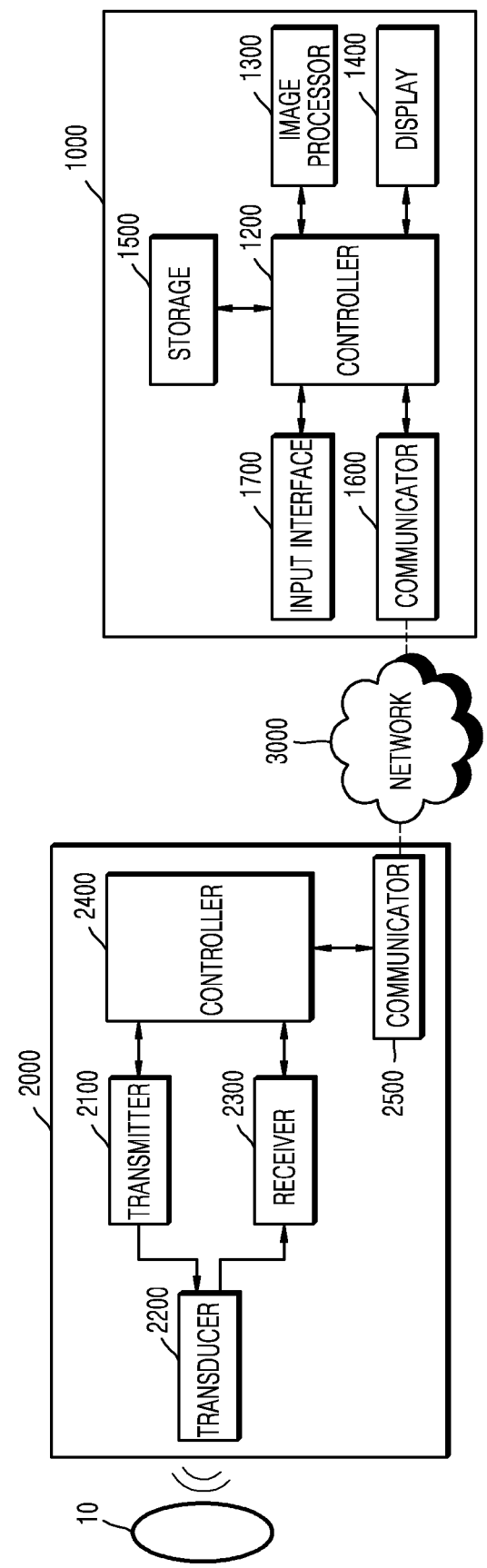
FIG. 10 is a block diagram illustrating configurations of a wireless ultrasound probe and an ultrasound diagnostic apparatus, according to an embodiment.

FIG. 10 is a block diagram of a configurations of a wireless ultrasound probe 2000 and an ultrasound diagnostic apparatus 1000 according to an embodiment.

Referring to FIG. 10, the ultrasound diagnostic apparatus 1000 may be connected to a wireless ultrasound probe 2000 via a network 3000.

The wireless ultrasound probe 2000 may include a transmitter 2100, a transducer 2200, a receiver 2300, a controller 2400, and a communicator 2500. Although FIG. 10 shows that the wireless ultrasound probe 2000 includes both the transmitter 2100 and the receiver 2300, according to an implemented configuration, the wireless ultrasound probe 2000 may include some of the components of the transmitter 2100 and the receiver 2300 while the ultrasound diagnostic apparatus 1000 may also include some of the components thereof.

The transducer 2200 may include a plurality of transducer elements. The plurality of transducer elements may transmit ultrasound signals to an object 10 in response to transmitted signals received from the transmitter 2100. The transducer elements may receive ultrasound signals reflected from the object 10 so as to generate reception signals.

The controller 2400 controls the transmitter 2100 to generate transmitting signals to be respectively applied to the transducer elements based on positions and focal points of the transducer elements.

The controller 2400 controls the receiver 2300 to generate ultrasound data by performing analog-to-digital conversion on the reception signals received from the transducer 2200 and summing the analog-to-digital converted reception signals based on a position and a focal point of the transducer elements.

The communicator 2500 may wirelessly transmit the generated ultrasound data or ultrasound image to the ultrasound diagnostic apparatus 1000 via a wireless network. Alternatively, the communicator 2500 may receive a control signal and data from the ultrasound diagnostic apparatus 1000.

The ultrasound diagnostic apparatus 1000 may receive ultrasound data or an ultrasound image from the wireless ultrasound probe 2000. The ultrasound diagnostic apparatus 1000 may include a controller 1200, an image processor 1300, a display 1400, and a storage 1500, a communicator 1600, and an input interface 1700.

The controller 1200 may control all operations of the ultrasound diagnostic apparatus 1000 and flow of signals between the internal elements of the ultrasound diagnostic apparatus 1000. The controller 1200 may include a memory for storing a program or data to perform functions of the ultrasound diagnostic apparatus 1000 and a processor for processing the program or data. Furthermore, the controller 1200 may control the operation of the ultrasound diagnostic apparatus 1000 by receiving a control signal from the input interface 1700 or an external apparatus.

The ultrasound diagnostic apparatus 1000 may include the communicator 1600 and may be connected to external apparatuses, for example, servers, medical apparatuses, and portable devices such as smart phones, tablet PCs, wearable devices, etc., via the communicator 1600.

The communicator 1600 may include at least one element capable of communicating with the external apparatuses. For example, the communicator 1600 may include at least one of a local area communication module, a wired communication module, and a wireless communication module.

The communicator 1600 may receive a control signal and data from an external apparatus and transmit the received control signal to the controller 1200 such that the controller 1200 may control the ultrasound diagnostic apparatus 1000 in response to the received control signal.

Alternatively, the controller 1200 may transmit a control signal to the external apparatus via the communicator 1600 so as to control the external apparatus in response to the control signal from the controller 1200.

For example, the external apparatus may process data from the external apparatus in response to the control signal from the controller 1200 received via the communicator 1600.

A program for controlling the ultrasound diagnostic apparatus 1000 may be installed in the external apparatus. The program may include instructions for performing part of operation of the controller 1200 or the entire operation thereof.

The program may be pre-installed in the external apparatus or may be installed by a user of the external apparatus by downloading the program from a server that provides applications. The server that provides applications may include a recording medium on which the program is stored.

The image processor 1300 may generate an ultrasound image by using ultrasound data received from the wireless ultrasound probe 2000.

The display 1400 may display an ultrasound image received from the wireless ultrasound probe 2000 and an ultrasound image generated by the ultrasound diagnostic apparatus 1000. The ultrasound diagnostic apparatus 1000 may include two or more displays 1400 according to its implemented configuration. Furthermore, the display 1400 may be combined with a touch panel to form a touch screen.

The storage 1500 may store various pieces of data or programs for driving and controlling the ultrasound diagnostic apparatus 1000, input and/or output ultrasound data, ultrasound images, etc.

The input interface 1700 receives a user input for controlling the ultrasound diagnostic apparatus 1000. For example, the user input may include an input for manipulating a button, a keypad, a mouse, a trackball, a jog switch, or a knob, an input for touching a touchpad or a touch screen, a voice input, a motion input, and an input of biometric information such as iris recognition or fingerprint recognition, but embodiments are not limited thereto.

Figure 11A:
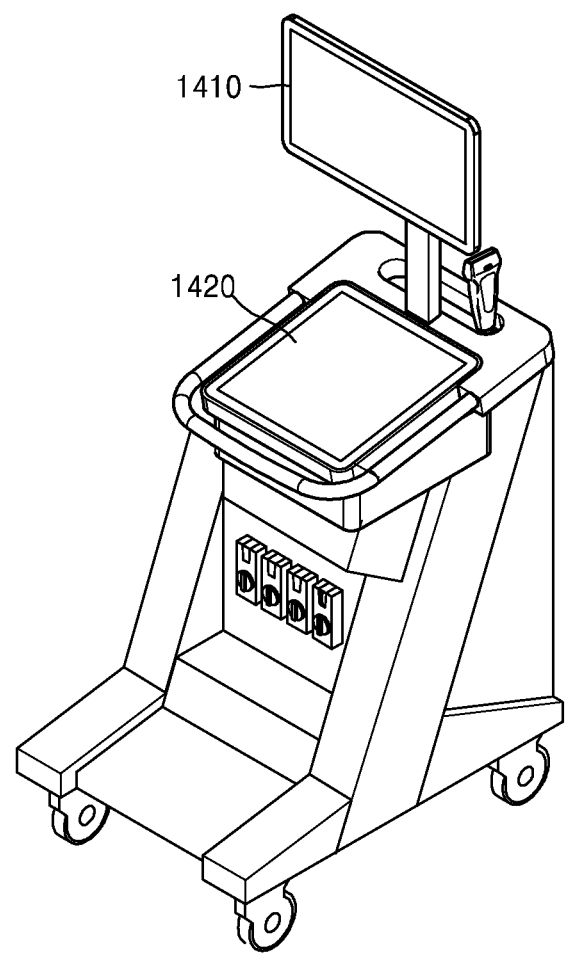
FIGS. 11A, 11B, and 11C are diagrams illustrating ultrasound diagnostic apparatuses, according to an embodiment.
Figure 11B:
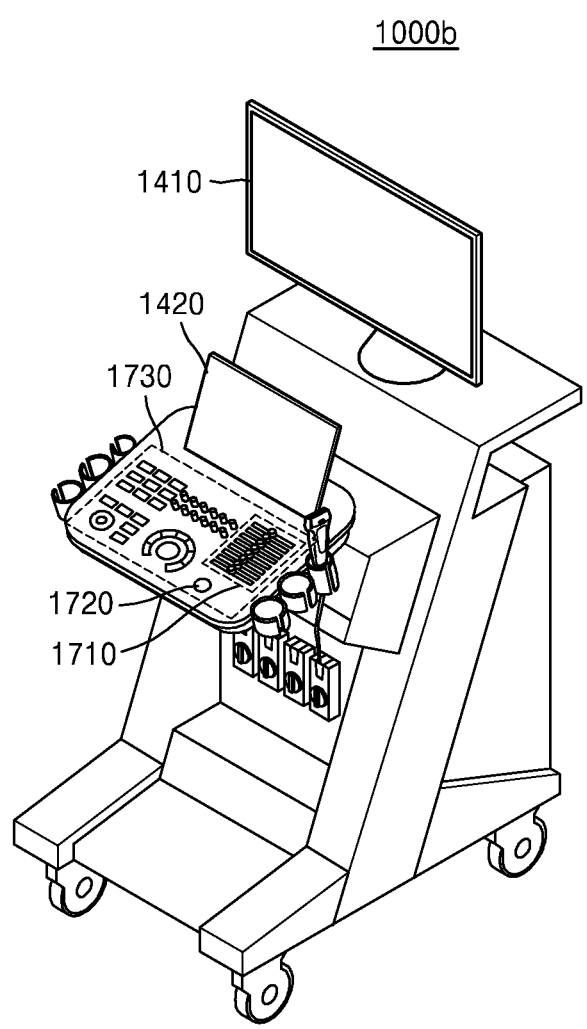
Figure 11C:
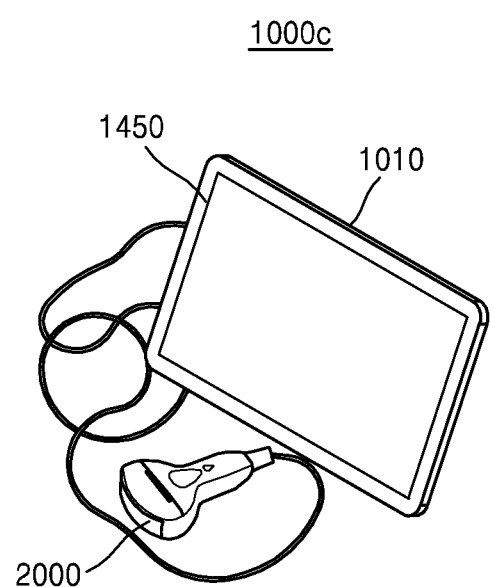

FIGS. 11A, 11B, and 11C are diagrams illustrating ultrasound diagnostic apparatuses, according to an embodiment.

Referring to FIGS. 11A and 11B, the ultrasound diagnostic apparatuses 1000a and 1000b may include a main display 1410 and a sub-display 1420. At least one among the main display 1410 and the sub-display 1420 may include a touch screen. The main display 1410 and the sub-display 1420 may display ultrasound images and/or various information processed by the ultrasound diagnostic apparatuses 1000a and 1000b. The main display 1410 and the sub-display 1420 may provide graphical user interfaces (GUI), thereby receiving user's inputs of data to control the ultrasound diagnostic apparatuses 1000a and 1000b. For example, the main display 1410 may display an ultrasound image and the sub-display 1420 may display a control panel to control display of the ultrasound image as a GUI. The sub-display 1420 may receive an input of data to control the display of an image through the control panel displayed as a GUI. The ultrasound diagnostic apparatuses 1000a and 1000b may control the display of the ultrasound image on the main display 1410 by using the input control data.

Referring to FIG. 11B, the ultrasound diagnostic apparatus 1000b may include a control panel 1730. The control panel 1730 may include buttons, trackballs, jog switches, or knobs, and may receive data to control the ultrasound diagnostic apparatus 1000b from the user. For example, the control panel 1730 may include a time gain compensation (TGC) button 1710 and a freeze button 1720. The TGC button 1710 is to set a TGC value for each depth of an ultrasound image. Also, when an input of the freeze button 1720 is detected during scanning an ultrasound image, the ultrasound diagnostic apparatus 1000b may keep displaying a frame image at that time point.

The buttons, trackballs, jog switches, and knobs included in the control panel 1730 may be provided as a GUI to the main display 1410 or the sub-display 1420.

Referring to FIG. 11C, the ultrasound diagnostic apparatus 1000c may be embodied as a portable ultrasound diagnostic apparatus. An example of the portable ultrasound diagnostic apparatus 1000c may include, for example, smart phones including probes and applications, laptop computers, personal digital assistants (PDAs), or tablet PCs, but an embodiment is not limited thereto.

The ultrasound diagnostic apparatus 1000c may include the probe 2000 and a main body 1010. The probe 2000 may be connected to one side of the main body 1010 by wire or wirelessly. The main body 1010 may include a touch screen 1450. The touch screen 1450 may display an ultrasound image, various pieces of information processed by the ultrasound diagnostic apparatus 1000c, and a GUI.

An ultrasound diagnostic apparatus according to the embodiments may detect a state in which supply of a charging power is discontinued, and may be automatically paired with a wireless ultrasound probe for which supply of the charging power is discontinued, such that, when a user wants to use the wireless ultrasound probe, the user can immediately use the wireless ultrasound probe without a separate pairing process with respect to the wireless ultrasound probe, user convenience may be improved.

The embodiments of the present disclosure can be written as computer programs and can be implemented in general-use digital computers that execute the programs using a computer-readable recording medium. The embodiments of the present disclosure may be embodied in form of a computer-readable recording medium for storing computer executable instructions and data. The instructions may be stored in form of program codes and, when executed by a processor, may perform a certain operation by generating a certain program module. Also, when executed by a processor, the instructions may perform certain operations of the disclosed embodiments.

Examples of the computer-readable recording medium include magnetic storage media (e.g., ROM, floppy disks, hard disks, etc.), optical recording media (e.g., CD-ROMs or DVDs), etc.

While the present disclosure has been particularly shown and described with reference to embodiments thereof, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. A wireless ultrasound probe wirelessly connected to an ultrasound diagnostic apparatus, the wireless ultrasound probe comprising:
   a first battery;
   a wireless communication module;
   a first charger configured to receive a charging power for charging the first battery from the ultrasound diagnostic apparatus; and
   a controller configured to detect a state in which the first charger is detached from a charging terminal of the ultrasound diagnostic apparatus to discontinue supply of the charging power, and to control the wireless communication module to be wirelessly paired with the ultrasound diagnostic apparatus,
   wherein the wireless ultrasound probe is mounted in a case including a second battery, a charging power supplier, and a second charger, and the first charger is further configured to receive, from the case, the charging power, and
   wherein the controller is further configured to:
      detect a state in which the wireless ultrasound probe is detached from the case to discontinue the supply of the charging power from the case, and
      control the wireless communication module to be wirelessly paired with the ultrasound diagnostic apparatus when the charging power from the case is discontinued.

2. The wireless ultrasound probe of claim 1, wherein, after the wireless ultrasound probe is paired with the ultrasound diagnostic apparatus, the controller is further configured to control the wireless communication module to transmit, to the ultrasound diagnostic apparatus, probe characteristic information comprising at least one of identification (ID) information of the wireless ultrasound probe, a type of the wireless ultrasound probe, a radio frequency range of use, depth value information, and remaining battery amount information.

3. The wireless ultrasound probe of claim 1, wherein the controller is further configured to:
   detect an activation signal indicating at least one of contact between the wireless ultrasound probe and an object, application of a gel with respect to the wireless ultrasound probe, motion of a user holding the wireless ultrasound probe, and a button input with respect to the wireless ultrasound probe, and
   activate, in response to the activation signal, the wireless ultrasound probe to transmit an ultrasound signal to the object.

4. An ultrasound diagnostic apparatus wirelessly connected to a wireless ultrasound probe, the ultrasound diagnostic apparatus comprising;
   a wireless communication module;
   a charging power supplier configured to supply a charging power to the wireless ultrasound probe; and
   a controller configured to detect a state in which the wireless ultrasound probe that has been charged is detached from the charging power supplier, causing supply of the charging power to the wireless ultrasound probe to be discontinued, and to control the wireless communication module to be wirelessly paired with the wireless ultrasound probe by using a wireless communication scheme,
   wherein the wireless ultrasound probe and the ultrasound diagnostic apparatus are mounted in a case including a case battery, the charging power supplier, and a charger, and the wireless ultrasound probe receives, from the case, the charging power for charging a battery of the wireless ultrasound probe, and
   wherein the controller is further configured to:
      detect a state in which the wireless ultrasound probe is detached from the case to discontinue the supply of the charging power from the case, and control the wireless communication module to be wirelessly paired with the wireless ultrasound probe when the charging power from the case is discontinued.

5. The ultrasound diagnostic apparatus of claim 4, wherein, in the state in which supply of the charging power to the wireless ultrasound probe is discontinued, the controller is further configured to control the wireless communication module to receive, from the paired wireless ultrasound probe, probe characteristic information comprising at least one of identification (ID) information of the wireless ultrasound probe, a type of the wireless ultrasound probe, a radio frequency range of use, depth value information, and remaining battery amount information.

6. The ultrasound diagnostic apparatus of claim 4, further comprising a display configured to display a user interface (UI) indicating, by using a text or an icon, probe characteristic information received from the wireless ultrasound probe.

7. The ultrasound diagnostic apparatus of claim 6, further comprising a memory storing system information and a preset of a UI pattern, wherein the system information is used to obtain an ultrasound image according to ID information and a type of the wireless ultrasound probe, and the preset is about a format of the ultrasound image, and
wherein the controller is further configured to load, from the memory, the preset based on the ID information and the type of the wireless ultrasound probe which is comprised in the probe characteristic information, and to display the loaded preset on the display.

8. The ultrasound diagnostic apparatus of claim 4, wherein the controller is further configured to:
detect an activation signal indicating at least one of contact between the wireless ultrasound probe and an object, application of a gel with respect to the wireless ultrasound probe, motion of a user holding the wireless ultrasound probe, and a button input with respect to the wireless ultrasound probe, and
transmit, in response to the activation signal, a beamforming control signal to the wireless ultrasound probe to transmit an ultrasound signal to the object.

9. A method, performed by an ultrasound diagnostic apparatus, of connecting the ultrasound diagnostic apparatus with a wireless ultrasound probe, the method comprising:
supplying a charging power to the wireless ultrasound probe;
detecting a state in which the wireless ultrasound probe is detached to discontinue supply of the charging power to the wireless ultrasound probe; and
performing pairing with the wireless ultrasound probe by using a wireless communication scheme,
wherein the wireless ultrasound probe and the ultrasound diagnostic apparatus are mounted in a case, and the wireless ultrasound probe receives, from the case including a case battery, a charging power supplier, and from a charger, the charging power for charging a battery of the wireless ultrasound probe, and
wherein the detecting of the state comprises detecting a state in which the wireless ultrasound probe is detached from the case to discontinue the supply of the charging power from the case, and
the performing of the pairing comprises performing wireless pairing with the wireless ultrasound probe when the supply of the charging power from the case to the wireless ultrasound probe is discontinued.

10. The method of claim 9, further comprising, in the state in which supply of the charging power to the wireless ultrasound probe is discontinued, receiving, from the paired wireless ultrasound probe, probe characteristic information comprising at least one of identification (ID) information of the wireless ultrasound probe, a type of the wireless ultrasound probe, a radio frequency range of use, depth value information, and remaining battery amount information.

11. The method of claim 10, further comprising displaying a user interface (UI) indicating, by using a text or an icon, the probe characteristic information received from the wireless ultrasound probe.

12. The method of claim 10, further comprising:
loading, from a memory of the ultrasound diagnostic apparatus, system information and a preset of a UI pattern, wherein the system information is used to obtain an ultrasound image according to the ID information and the type of the wireless ultrasound probe which are comprised in the probe characteristic information, and the preset is about a format of the ultrasound image; and
displaying the loaded preset.

13. The method of claim 9, further comprising, after the pairing:
detecting an activation signal indicating at least one of contact between the wireless ultrasound probe and an object, application of a gel with respect to the wireless ultrasound probe, motion of a user holding the wireless ultrasound probe, and a button input with respect to the wireless ultrasound probe; and
activating, in response to the activation signal, the wireless ultrasound probe to transmit an ultrasound signal to the object.

14. A non-transitory computer-readable recording medium having recorded thereon a program to be executed on a computer, the recording medium comprising instructions to perform:
supplying a charging power to a wireless ultrasound probe;
detecting a state in which the wireless ultrasound probe is detached from a charging terminal of an ultrasound diagnostic apparatus, causing supply of the charging power to the wireless ultrasound probe to be discontinued; and
performing wireless pairing between the ultrasound diagnostic apparatus and the wireless ultrasound probe,
wherein the wireless ultrasound probe and the ultrasound diagnostic apparatus are mounted in a case including a case battery, a charging power supplier, and a charger, and the wireless ultrasound probe receives, from the case, the charging power for charging a battery of the wireless ultrasound probe, and
wherein the detecting of the state comprises detecting a state in which the wireless ultrasound probe is detached from the case to discontinue the supply of the charging power from the case, and
the performing of the pairing comprises performing wireless pairing with the wireless ultrasound probe when the supply of the charging power from the case to the wireless ultrasound probe is discontinued.

\* \* \* \* \*